US00PP21787P2

(12) United States Plant Patent
Verschoor

(10) Patent No.: US PP21,787 P2
(45) Date of Patent: Mar. 15, 2011

(54) ***PHLOX* PLANT NAMED "AUREOLE"**

(50) Latin Name: *Phlox paniculata*
Varietal Denomination: Aureole

(76) Inventor: Jan Verschoor, Haarlem (NL)

( * ) Notice: Subject to any disclaimer, the term of this patent is extended or adjusted under 35 U.S.C. 154(b) by 0 days.

(21) Appl. No.: 12/590,881

(22) Filed: Nov. 16, 2009

(51) Int. Cl.
*A01H 5/00* (2006.01)

(52) U.S. Cl. ..... Plt./320

(58) Field of Classification Search ..... Plt./320
See application file for complete search history.

(56) References Cited

U.S. PATENT DOCUMENTS

PP16,059 P2 * 10/2005 Vester ..... Plt./320

* cited by examiner

*Primary Examiner*—Wendy Haas
(74) *Attorney, Agent, or Firm*—Penny J. Aguirre

(57) ABSTRACT

A new cultivar of *Phlox*, 'Aureole', characterized by its flowers that are bright pink in color with yellow-green margins at the apex of each petal, its large flowers, its healthy foliage with a high degree of mildew resistance, and its compact plant habit with sturdy stems.

2 Drawing Sheets

Botanical classification: *Phlox paniculata.*
Cultivar designation: 'Aureole'.

BACKGROUND OF THE INVENTION

The present invention relates to a new and distinct cultivar of *Phlox* plant, botanically known as *Phlox paniculata* 'Aureole' and will be referred to hereafter by its cultivar name, 'Aureole'. The new cultivar represents a new herbaceous perennial grown for landscape use.

The Inventor selected the new cultivar as a single unique plant in a trial plot in Haarlem, The Netherlands in summer of 2007. 'Aureole' was selected from the results of an open pollination of unnamed proprietary plants of *Phlox paniculata* and the parentage is unknown.

Asexual reproduction of the new cultivar was first accomplished by stem cuttings in Haarlem, The Netherlands in summer of 2007 by the Inventor. It has been determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Aureole' from other varieties of *Phlox* known to the Inventor.

1. 'Aureole' exhibits flowers that are bright pink in color with a light yellow-green margin at apex of each petal.
2. 'Aureole' exhibits large flowers that are up to 2 cm in diameter.
3. 'Aureole' exhibits healthy foliage with a high degree of mildew resistance.
4. 'Aureole' exhibits a compact plant habit with sturdy stems.

The closest comparison plant to 'Aureole' is 'Sherbert Cocktail' (not patented), which is similar to 'Aureole' in having flowers that are pink with yellow margins. 'Sherbert Cocktail' differs from 'Aureole' in being less compact, in having smaller flowers that have centers that are lighter pink to white in color, in having a less compact habit, and in having weaker stems. There are no other cultivars known to the Inventor that are similar to 'Aureole' in flower coloration.

BRIEF DESCRIPTION OF THE DRAWING

The accompanying colored photographs illustrate the overall appearance and distinct characteristics of the new *Phlox.* The photographs were taken of a one year-old plant of 'Aureole' as grown a trial garden in a garden in Haarlem, The Netherlands.

The photograph in FIG. 1 is a view of a plant of 'Aureole' in bloom.

Figure 1:
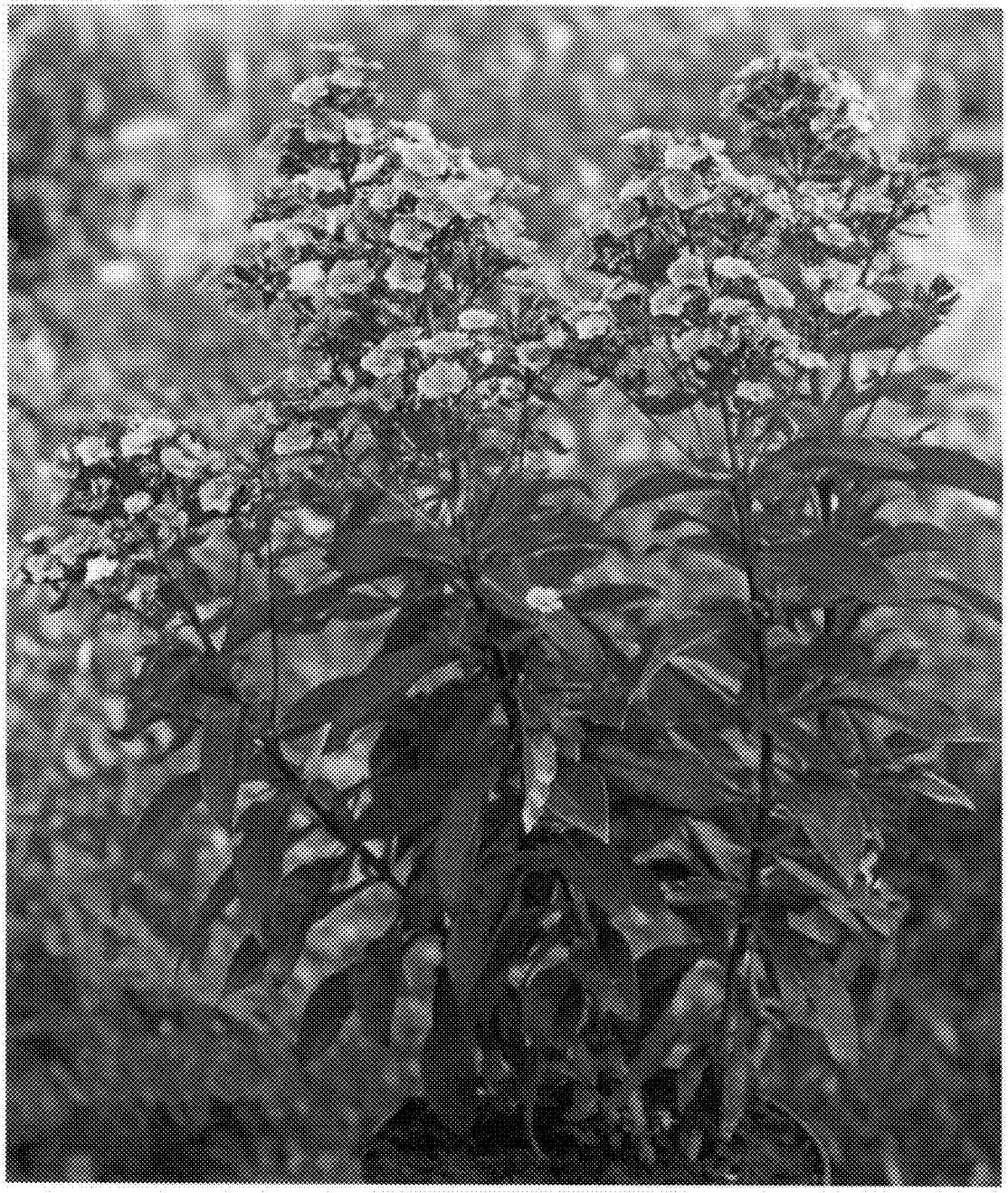
Figure 2:
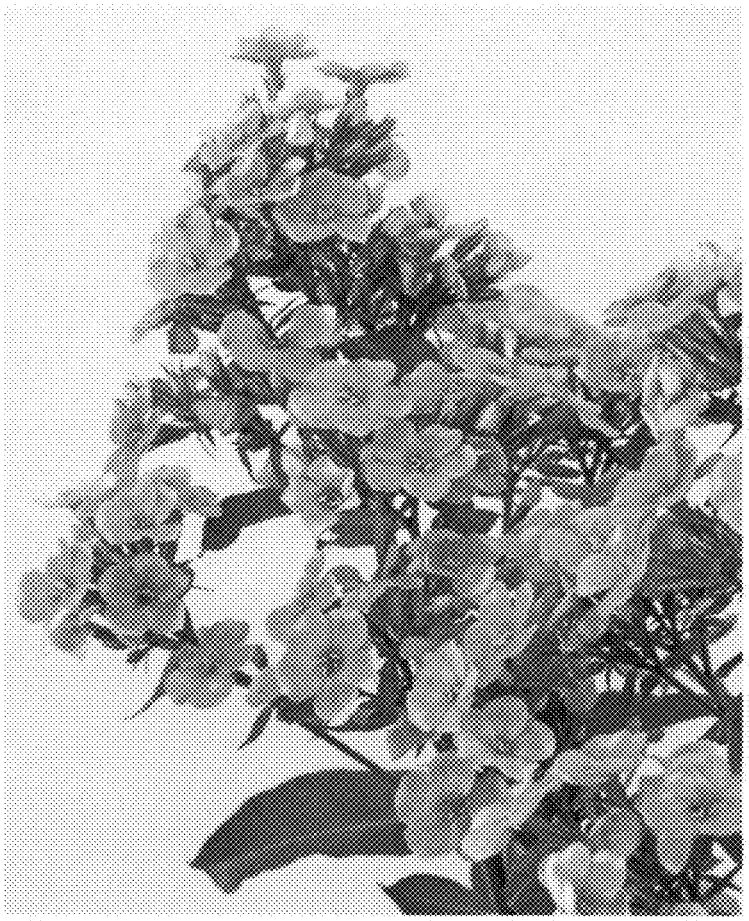

The photograph in FIG. 2 is a close-up view of an inflorescence of 'Aureole'.

Figure 3:
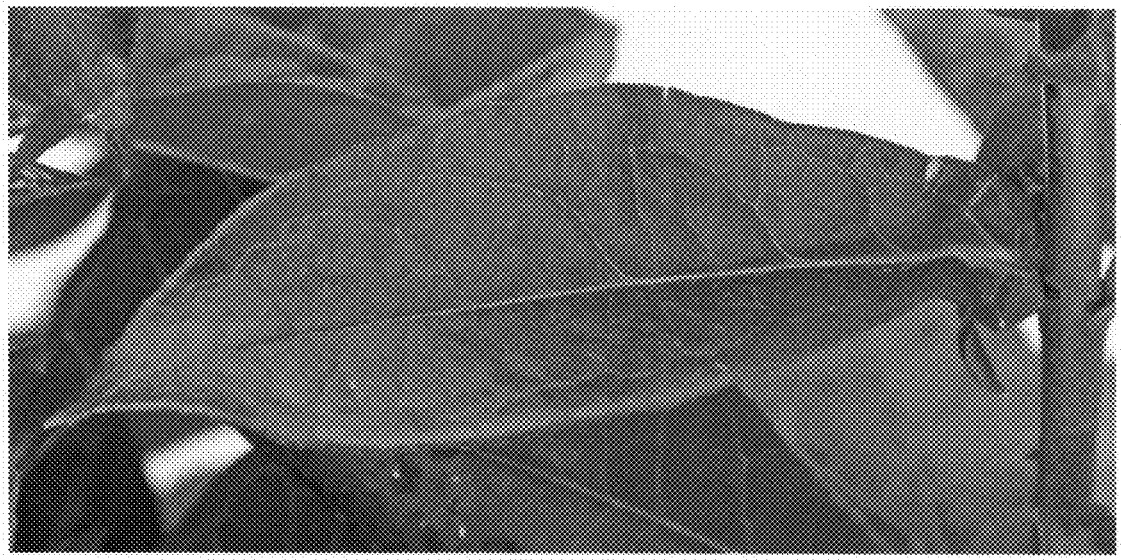

The Photograph in FIG. 3 provides a close-up view of a leaf of 'Aureole'.

The colors in the photograph may differ slightly from the color values cited in the detailed botanical description, which accurately describe the colors of the new *Phlox.*

DETAILED BOTANICAL DESCRIPTION OF THE PLANT

The following is a detailed description of one year-old plants of the new cultivar as grown outdoors in a trial plot in Haarlem, The Netherlands. The plants were grown under average day temperatures of 15° C. to 32° C. and average night temperatures of 8° C. to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

*Blooming period.*—Mid to late summer in the Netherlands.

*Plant habit.*—Herbaceous perennial, upright.

*Height and spread.*—Reaches about 54 cm in height and about 40 cm in spread.

*Cold hardiness.*—At least in U.S.D.A. Zone 4.

*Diseases and pests.*—Has shown good resistance to powdery mildew.

*Root description.*—Fibrous.

Growth and propagation:

*Growth rate.*—Moderate.

*Propagation.*—Stem cuttings, division also possible.

Stem description:

*Stem size.*—An average of 33.3 cm in length and 5 mm in width.

*Stem shape.*—Round.

*Stem strength.*—Strong and sturdy.

*Stem color.*—146A.

*Stem surface.*—Glabrous, slightly glossy.

*Stem aspect.*—Held nearly upright.

*Internode length.*—An average of 2.1 cm.

*Branching habit.*—Flowering stems emerge from crown, an average of 5 stems per plant one year in age, no lateral branches.

Foliage description:

*Leaf shape.*—Narrowly obovate to narrowly elliptic.

*Leaf division.*—Simple.

*Leaf base.*—Truncate.

*Leaf apex.*—Narrowly acute.

*Leaf venation.*—Pinnate, not conspicuous, 144B and 144C on upper surface and lower surface.

*Leaf margins.*—Slightly revolute, very finely serrate (about 30 serrations per cm).

*Leaf attachment.*—Petiolate.

*Leaf arrangement.*—Opposite.

*Leaf surface.*—Smooth and glabrous on upper and lower surface.

*Leaf color.*—Upper surface newly formed; 143A to 143B, lower surface newly formed; 143C, upper surface mature; N137A and 147A, lower surface mature; 137B.

*Leaf size.*—An average of 10.3 cm in length and 3.5 cm in width.

*Leaf quantity.*—An average of 32 per stem.

*Leaf fragrance.*—None.

*Petioles.*—V-shaped, an average of 4 mm in width and 3 mm in length, 144B to 144C in color, surface is glabrous.

Flower description:

*Inflorescence type.*—Compound terminal panicle.

*Lastingness of inflorescence.*—About 3 to 4 weeks from the opening of the first flower to senescence of last flower, individual flower lasts about 10 days.

*Inflorescence size.*—An average of 20.1 cm in height and 15.8 cm in diameter.

*Flower fragrance.*—Faint to moderate, sweet phlox fragrance.

*Flower number.*—Average of 200 per inflorescence, one inflorescence per flowering stem.

*Flower aspect.*—Upright to outward, dependant on location of the inflorescence.

*Flower bud.*—An average of 1.4 cm in length and up to 9 mm in width, obovate in shape, 145C and 145D in color and flushed with N77C with calyx portion 148A and 148B and strongly tinged with N186C.

*Flower form.*—Explanate with tubular base.

*Flower size.*—An average of 2.2 cm in length and 2.2 cm in width.

*Corolla tube.*—About 1.4 cm in length, 3 mm in width, color N77C to N77D on outer and inner surface, dull and smooth surface.

*Corolla lobes.*—5, orbicular in shape, held horizontally when fully open, slightly overlapping, about 1 cm in length and width, apex rounded, base fused to tube, entire margins, upper surface color when opening; N74B with apex 145C, lower surface color when opening; 75B to 75C, upper surface color when fully open; 67B with apex 145C to 145D, lower surface color when fully open; 75C, non-fading, surface is dull and smooth on upper and lower surface.

*Calyx.*—Campanulate in form, comprised of fused sepals with sepal tips free, an average of 1.1 cm in length and 9 mm in width.

*Sepals.*—5, primarily fused with free tips, linear in shape, margins entire, base fused (about 18%), apex narrowly apiculate, an average of 1.1 cm in length and 1.5 mm in width, surface is smooth and moderately glossy, color of newly open flowers upper and lower surface; 148A to 148B and strongly tinged with N186C, color of fully open flowers upper and lower surface; 147A and 148A but slightly darker.

*Peduncles.*—Oval in shape, strong, primary an average of 16.7 cm in length and 3 mm in width, secondary an average of 6.3 cm in length and 1.5 mm in width, primary held upright, secondary held at about a 35° angle, glabrous surface, color 146C.

*Pedicels.*—Oval in shape, strong, an average of 7 mm in length and 1 mm in width, glabrous surface, color 146C.

Reproductive organs:

*Gynoecium.*—1 pistil, stigma has 3 branches about 1.8 cm in length and 150D in color, style is about 1.6 cm in length and N77C to N77D in color, ovary is inferior and 143A in color.

*Androcoecium.*—5 stamens, anthers are basifixed, oblong in shape, 1.5 mm in length and 162C in color, filaments are adnate to petals and 1 mm in length, pollen is low in quantity and ranges from 11C to 11D to 162C in color.

*Seeds.*—None observed.

It is claimed:

1. A new and distinct cultivar of *Phlox* plant named 'Aureole' as herein illustrated and described.

* * * * *